May 19, 1953 R. W. DAILEY Plant Pat. 1,190
CAMELLIA PLANT
Filed July 23, 1947
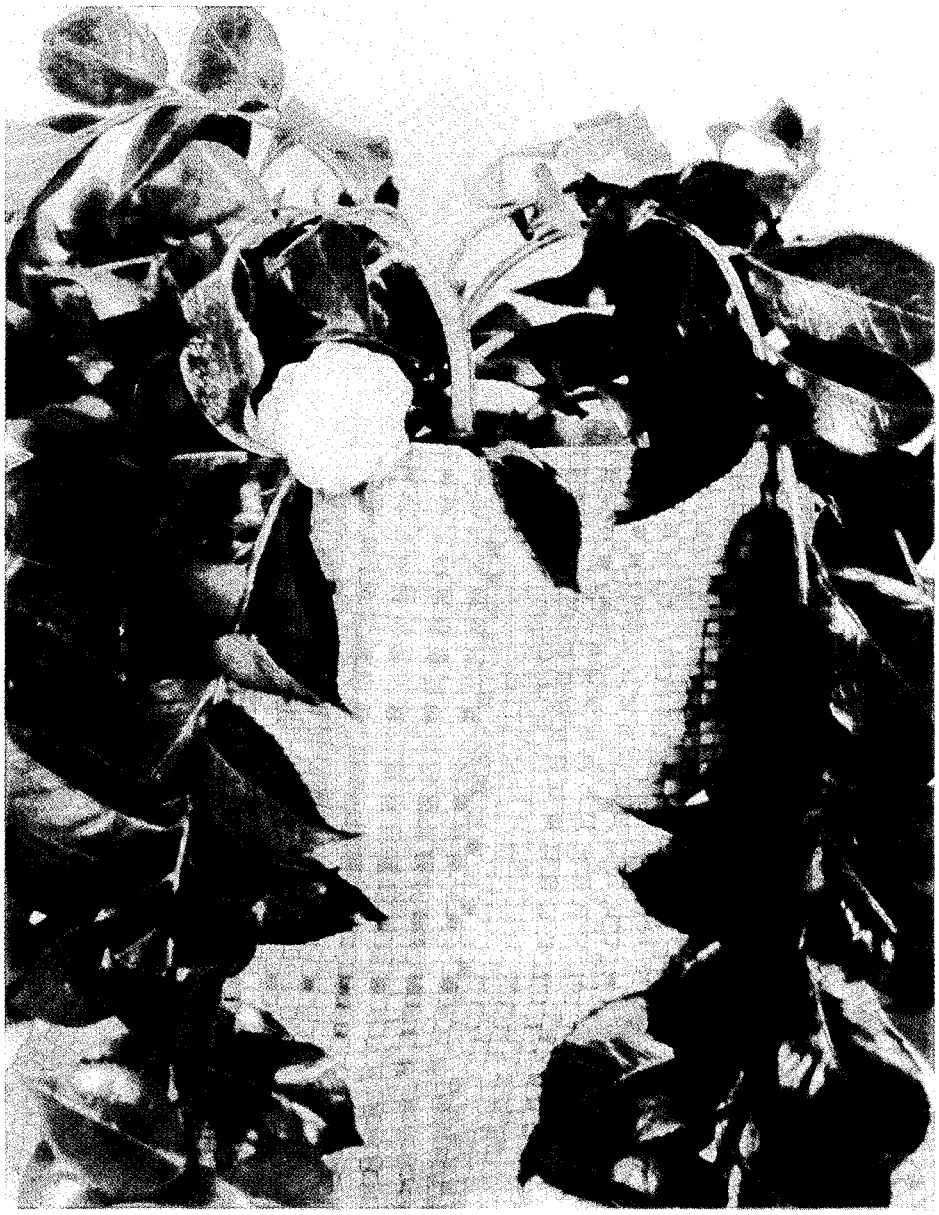
INVENTOR
Roland W. Dailey
By J. E. Trabucco
Attorney Patented May 19, 1953

Plant Pat. 1,190

UNITED STATES PATENT OFFICE 1,190

CAMELLIA PLANT

Roland W. Dailey, San Jose, Calif.

Application July 23, 1947, Serial No. 763,018

1 Claim. (Cl. 47—60)

This invention relates to a new and distinctive camellia plant of the Japonica type.

An object of my invention is to provide a new and distinctive variety of camellia plant having a number of characteristics not found in plants of this kind.

The accompanying colored drawing shows a specimen of the flower and foliage of my new camellia plant.

The camellia plant constituting the subject matter of the invention is entirely unlike other known camellia plants, in that its branches are quite slender and assume downwardly drooping positions. The plant is definitely of the pendulous type, and its blossoms face downwardly. During the unusually long blooming period from January to March, blossoms appear along substantially the entire length of the branches.

The blossoms of my camellia plant are medium red in color until full bloom is reached, and thereafter they assume a lighter red color with a lavender tint appearing along their veins.

The leaves of my camellia plant are large in size and are particularly characterized by their dark green color and glossy appearance. The blossoms assume what is commonly known as a full rose form.

Referred to Maerz and Paul's Dictionary of Color (1930) the medium red mentioned above is 1–K–8, Rose Doree; the lavender, 43–C–5; the dark green is 30–L–2, Michigan Green, to 31–L–1, Myrtle Green.

This variety of camellia plant originated as a seedling produced by me, by cross-pollination, after and through much experimentation with different well known varieties of camellia plants with a view of developing a new variety of pendulous type. Asexual reproduction by cuttings and grafting at San Jose, California, shows that the foregoing characteristics were reproduced true to type.

The growth of my camellia plant is quite rapid and the flower buds usually appear along the pendulous branches but seldom at their tips. The flowers grown on my camellia plant vary in that some of them are complete double with perfect centers while others are complete double with divided centers. The form of the said flowers resembles the well known unpatented Pope Pius camellia and they vary in size from three to three and three-quarters inches in diameter. The flowers each ordinarily have from about thirty-four to forty-five petals.

I claim:

A new and distinct variety of camellia plant substantially as herein disclosed, characterized as to novelty by its slender pendulous branches, its habit of putting out blossoms along a substantial portion of the branches, and the formation of the blossoms in downwardly facing positions.

ROLAND W. DAILEY.

No references cited.